(12) United States Patent
Blum et al.

(10) Patent No.: US 9,272,153 B2
(45) Date of Patent: *Mar. 1, 2016

(54) VOA GENERATION SYSTEM AND METHOD USING A FIBER SPECIFIC ANALYSIS

(71) Applicant: BOSTON SCIENTIFIC NEUROMODULATION CORPORATION, Valencia, CA (US)

(72) Inventors: David Arthur Blum, Boston, MA (US); Michael A. Moffitt, Valencia, CA (US); Karl Steinke, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/557,640

(22) Filed: Dec. 2, 2014

(65) Prior Publication Data

US 2015/0088223 A1  Mar. 26, 2015

Related U.S. Application Data

(63) Continuation-in-part of application No. 13/507,962, filed on Aug. 9, 2012, and a continuation-in-part of application No. 12/454,340, filed on May 15, 2009, now Pat. No. 9,072,905.

(Continued)

(51) Int. Cl.
*A61N 1/36* (2006.01)
*A61N 1/372* (2006.01)

(Continued)

(52) U.S. Cl.
CPC ........ *A61N 1/37241* (2013.01); *A61N 1/36082* (2013.01); *A61N 1/37247* (2013.01);

(Continued)

(58) Field of Classification Search
CPC ............ A61N 1/0534; A61N 1/36185; A61N 1/37247
See application file for complete search history.

(56) References Cited

U.S. PATENT DOCUMENTS 5,099,846 A   3/1992  Hardy
5,361,763 A   11/1994 Kao et al.

(Continued)

FOREIGN PATENT DOCUMENTS

WO     01/90876 A1    11/2001
WO   2004/019799 A2    3/2004

(Continued)

OTHER PUBLICATIONS

European Patent Office, International Searching Authority, International Search Report and the Written Opinion of the ISA in International Application No. PCT/US2011/040329, dated Dec. 29, 2011, 14 pages.

(Continued)

*Primary Examiner* — Joseph Dietrich
(74) *Attorney, Agent, or Firm* — Lowe Graham Jones PLLC; Bruce E. Black

(57) ABSTRACT

A system and method for generating an estimated volume of activation (VOA) corresponding to settings applied to a stimulation leadwire includes a processor performing the following: determining, for each of a plurality of neural elements, one or more respective parameters characterizing an electrical distribution along the neural element, looking up the one or more parameters for each of the neural elements in a look-up table (LUT), obtaining threshold values for each of the neural elements recorded in the LUT in association with the looked-up parameters, comparing, for each of the neural elements, a value of the leadwire settings to each of the respective threshold value, estimating based on the comparisons which of the neural elements would be activated by the settings, and generating a structure corresponding to a region including the neural elements estimated to be activated.

11 Claims, 6 Drawing Sheets
(2 of 6 Drawing Sheet(s) Filed in Color)

Related U.S. Application Data

(60) Provisional application No. 61/521,583, filed on Aug. 9, 2011, provisional application No. 61/690,270, filed on Jun. 22, 2012, provisional application No. 61/201,037, filed on Dec. 4, 2008, provisional application No. 61/113,927, filed on Nov. 12, 2008, provisional application No. 61/111,523, filed on Nov. 5, 2008, provisional application No. 61/079,362, filed on Jul. 9, 2008, provisional application No. 61/055,398, filed on May 22, 2008, provisional application No. 61/053,449, filed on May 15, 2008.

(51) Int. Cl.
  *A61N 1/05* (2006.01)
  *G06F 19/00* (2011.01)

(52) U.S. Cl.
  CPC ............ *A61N1/0534* (2013.01); *A61N 1/36185* (2013.01); *G06F 19/3437* (2013.01); *G06F 19/3481* (2013.01)

(56) References Cited

U.S. PATENT DOCUMENTS

| | | |
|---|---|---|
| 5,452,407 A | 9/1995 | Crook |
| 5,724,985 A | 3/1998 | Snell et al. |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,734,340 B2 | 6/2010 | De Ridder |
| 7,826,902 B2 | 11/2010 | Stone et al. |
| 7,848,802 B2 | 12/2010 | Goetz et al. |
| 8,180,601 B2 | 5/2012 | Butson et al. |
| 8,452,415 B2 | 5/2013 | Goetz et al. |
| 8,606,360 B2 | 12/2013 | Butson et al. |
| 8,620,452 B2 | 12/2013 | King et al. |
| 2004/0034394 A1 | 2/2004 | Woods et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0171587 A1 | 8/2005 | Daglow et al. |
| 2005/0228250 A1 | 10/2005 | Bitter et al. |
| 2006/0017749 A1 | 1/2006 | McIntyre et al. |
| 2006/0020292 A1 | 1/2006 | Goetz et al. |
| 2006/0094951 A1 | 5/2006 | Dean et al. |
| 2006/0235472 A1 | 10/2006 | Goetz et al. |
| 2006/0259079 A1 | 11/2006 | King |
| 2007/0043268 A1 | 2/2007 | Russell |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0123923 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |

(56) References Cited

U.S. PATENT DOCUMENTS

| | | | |
|---|---|---|---|
| 2008/0183256 | A1 | 7/2008 | Keacher |
| 2008/0188734 | A1 | 8/2008 | Suryanarayanan et al. |
| 2008/0215118 | A1 | 9/2008 | Goetz et al. |
| 2008/0269588 | A1 | 10/2008 | Csavoy et al. |
| 2008/0300654 | A1 | 12/2008 | Lambert et al. |
| 2009/0054950 | A1 | 2/2009 | Stephens |
| 2009/0082640 | A1 | 3/2009 | Kovach et al. |
| 2009/0082829 | A1 | 3/2009 | Panken et al. |
| 2009/0112289 | A1 | 4/2009 | Lee et al. |
| 2009/0149917 | A1 | 6/2009 | Whitehurst et al. |
| 2009/0196471 | A1 | 8/2009 | Goetz et al. |
| 2009/0196472 | A1 | 8/2009 | Goetz et al. |
| 2009/0198306 | A1 | 8/2009 | Goetz et al. |
| 2009/0204192 | A1 | 8/2009 | Carlton et al. |
| 2009/0276008 | A1 | 11/2009 | Lee et al. |
| 2009/0281595 | A1 | 11/2009 | King et al. |
| 2009/0281596 | A1 | 11/2009 | King et al. |
| 2009/0287271 | A1 | 11/2009 | Blum et al. |
| 2009/0287272 | A1 | 11/2009 | Kokones et al. |
| 2009/0287273 | A1 | 11/2009 | Carlton et al. |
| 2009/0287467 | A1 | 11/2009 | Sparks et al. |
| 2009/0299164 | A1 | 12/2009 | Singhal et al. |
| 2009/0299165 | A1 | 12/2009 | Singhal et al. |
| 2009/0299380 | A1 | 12/2009 | Singhal et al. |
| 2010/0010646 | A1 | 1/2010 | Drew et al. |
| 2010/0023103 | A1 | 1/2010 | Elborno |
| 2010/0023130 | A1 | 1/2010 | Henry et al. |
| 2010/0030312 | A1 | 2/2010 | Shen |
| 2010/0049276 | A1 | 2/2010 | Blum et al. |
| 2010/0049280 | A1 | 2/2010 | Goetz |
| 2010/0135553 | A1 | 6/2010 | Joglekar |
| 2010/0137944 | A1 | 6/2010 | Zhu |
| 2010/0179562 | A1 | 7/2010 | Linker et al. |
| 2011/0172737 | A1 | 7/2011 | Davis et al. |
| 2011/0191275 | A1 | 8/2011 | Lujan et al. |
| 2011/0307032 | A1 | 12/2011 | Goetz et al. |
| 2012/0265268 | A1 | 10/2012 | Blum et al. |
| 2012/0302912 | A1 | 11/2012 | Moffitt et al. |

FOREIGN PATENT DOCUMENTS

| | | | |
|---|---|---|---|
| WO | 2007/097859 | A1 | 8/2007 |
| WO | 2007/097861 | A1 | 8/2007 |
| WO | 2007/100427 | A1 | 9/2007 |
| WO | 2007/100428 | A1 | 9/2007 |
| WO | 2007/112061 | A2 | 10/2007 |
| WO | 2009097224 | A1 | 8/2009 |
| WO | 2010/120823 | A2 | 10/2010 |
| WO | 2011/139779 | A1 | 11/2011 |
| WO | 2011/159688 | A2 | 12/2011 |

OTHER PUBLICATIONS

European Patent Office, International Searching Authority, International Search Report and the Written Opinion of the ISA in International Application No. PCT/US2012/069667, dated Feb. 27, 2013, 15 pages.
European Patent Office, International Searching Authority, Partial International Search Report of the ISA in International Application No. PCT/US2013/056981, mailed May 6, 2014, 4 pages.
European Patent Office, International Search Report and the Written Opinion of the ISA in International Application No. PCT/US2013/056975, mailed Feb. 20, 2014, 11 pages.
European Patent Office, International Search Report and the Written Opinion of the ISA in International Application No. PCT/US2013/056984, mailed Dec. 10, 2013, 11 pages.
European Patent Office, International Search Report and the Written Opinion/ISA in International Patent Application No. PCT/US2013/056112, mailed May 15, 2014, 14 pages.
European Patent Office, International Search Report in International Application No. PCT/US2012/053344, dated Nov. 26, 2012, 8 pages.
European Patent Office, International Search Report in International Application No. PCT/US2012/050181, dated Jan. 3, 2013, 7 pages.
Euopean Patent Office, International Search Report and the Written Opinion in International Application No. PCT/US2012/050170, dated Oct. 5, 2012, 15 pages.
European Patent Office, International Search Report in International Application No. PCT/US09/03017, dated Aug. 3, 2009, 7 pages.
European Patent Office, International Search report and Written Opinion in PCT application No. PCT/US12/050174, dated Mar. 6, 2013, 20 pages.
European Patent Office, International Search Report and Written Opinion in International Application No. PCT/US2012/050187, dated Feb. 27, 2013, 9 pages.
European Patent Office, International Search Report and Written Opinion in International Application No. PCT/US2012/030700, dated Feb. 27, 2013, 9 pages.
European Patent Office, International Search Report in International Application No. PCT/US09/03041, dated Aug. 20, 2009, 7 pages.
European Patent Office, International Search Report and the Written Opinion of the International Searching Authority in International Application No. PCT/US2012/050175, dated Oct. 26, 2012, 15 pages.
European Patent Office, International Search Report in International Application No. PCT/US09/03038, dated Oct. 8, 2009, 9 pages.
European Patent Office, International Search Report in International Application No. PCT/US09/03040, dated Aug. 13, 2009, 7 pages.
European Patent Office, International Search Report in International Application No. PCT/US09/03049, dated Jan. 26, 2010, 8 pages.
European Patent Office, partial International Search Report in International Application No. PCT/US2012/030701, dated Feb. 15, 2013, 7 pages.
European Patent Office, partial International Search Report in International Application No. PCT/US2012/030705, dated Mar. 6, 2013, 7 pages.
Butson et al., "Current Steering to Control the Volume of Tissue Activated During Deep Brain Stimulation," Brain Stimulation 1, 2008, pp. 7-15.
Butson et al., "Patient Specific Analysis of the volume of tissue activated during deep brain stimulation," NeuroImage, Academic Press, vol. 34, No. 2, Dec. 2, 2006, pp. 661-670.
Butson et al., "Role of Electrode Design on the Volume of Tissue Activated During Deep Brain Stimulation," Journal of Neural Engineering, Mar. 1, 2006, vol. 3, No. 1, pp. 1-8.
Butson et al., "StimExplorer: Deep Brain Stimulation Parameter Selection Software System," Acta Neurochirugica, Jan. 1, 2007, vol. 97, No. 2, pp. 569-574.
Carnevale, N.T. et al., "The NEURON Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi A et al: "Patient-specific models of deep brain stimulation: Influence of field model complexity on neural activation predictions." Brain Stimulation, Elsevier, Amsterdam, NL, vol. 3, No. 2, Apr. 2010, pp. 65-77.
Commowick, Olivier et al., "Using Frankenstein's Creature Paradigm to Build a Patient Specific Atlas," Sep. 20, 2009, Medical Image Computing and Computer-Assisted Intervention, pp. 993-1000.
Cover, T.M. et al., "Elements of information theory," (1991) John Wiley & Sons, New York, NY, pp. 1-542.
Dice, Lee R., "Measures of the Amount of Ecologic Association Between Species," Ecology 26(3) (1945), pp. 297-302. doi:10.2307/1932409, http://jstor.org/stable/1932409.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Frankemolle, et al., "Reversing cognitive-motor impairments in Parkinson's disease patients using a computational modelling approach to deep brain stimulation programming," Brain 133 (2010), pp. 746-761.
Hubert, Lawrence et al., "Comparing partitions," Journal of Classification 2(1) (1985), pp. 193-218, doi:10.1007/BF01908075.

(56) References Cited

OTHER PUBLICATIONS

Izad, Olivier, "Computationally Efficient Method in Predicating Axonal Excitation," Dissertation for Masters Degree, Department of Biomedical Engineering, Case Western Reserve University, May 2009, 144 pages.

Jaccard, Paul, "Étude comparative de la distribution florale dans une portion odes Aples et des Jura," Bulletin de la Société Vaudoise des Sciences Naturelles (1901), vol. 37, pp. 547-579.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.

Lotjonen J.M.P. et al, "Fast and robust multi-atlas segmentation of brain magnetic resonance images," NeuroImage, Academic Press, vol. 49, No. 3, Feb. 1, 2010, pp. 2352-2365.

McIntyre, C. C., et al., "Modeling the excitability of mammalian nerve fibers: influence of afterpotentials on the recovery cycle," J Neurophysiol, 87(2) (Feb. 2002), pp. 995-1006.

Meila, Marina, "Comparing Clusterings by the Variation of Information," Learning Theory and Kernel Machines (2003), pp. 173-187.

Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Peterson, et al., "Predicting myelinated axon activation using spatial characteristics of the extracellular field," Journal of Neural Engineering, 8 (2011), 12 pages.

Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Schmidt et al., "Sketching and Composing Widgets for 3D Manipulation," Eurographics, Apr. 2008, vol. 27, No. 2, pp. 301-310.

Shen, Kaikai, et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Volkmann, J , et al., "Introduction to the programming of deep brain stimulators," Mov. Disord., vol. 17 (Suppl 3) (2002), pp. 181-187.

Warman, et al., "Modeling the Effects of Electric Fields on nerve Fibers: Determination of Excitation Thresholds," IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2, Jun. 1998, pp. 200-207.

VOA GENERATION SYSTEM AND METHOD USING A FIBER SPECIFIC ANALYSIS

CROSS-REFERENCE TO RELATED APPLICATIONS

The present application is a continuation-in-part of U.S. patent application Ser. No. 13/507,962 ("the '962 application"), filed Aug. 9, 2012, which claims priority to U.S. Provisional Patent Application Ser. Nos. 61/521,583 ("the '583 application"), filed Aug. 9, 2011 and 61/690,270 ("the '270 application"), filed Jun. 22, 2012. The present application is also a continuation-in-part of U.S. patent application Ser. No. 12/454,340 ("the '340 application"), filed May 15, 2009, which claims priority to U.S. Provisional Patent Application Ser. Nos. 61/201,037 ("the '037 application"), filed Dec. 4, 2008, 61/113,927 ("the '927 application"), filed Nov. 12, 2008, 61/111,523 ("the '523 application"), filed Nov. 5, 2008, 61/079,362 ("the '362 application"), filed Jul. 9, 2008, 61/055,398 ("the '398 application"), filed May 22, 2008 and 61/053,449 ("the '449 application"), filed May 15, 2008. The contents of all of the '962, '583, '270, '340, '037, '927, '523, '362, '398, and '449 applications are incorporated by reference herein in their entireties.

FIELD OF THE INVENTION

The present invention relates to a system and method for determining, on a fiber by fiber basis, a volume of activation (VOA) estimated to result from an anatomical stimulation by a stimulation leadwire having applied thereto clinician-specified stimulation parameter settings.

BACKGROUND

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, peripheral field stimulation therapy, sacral root stimulation therapy, or other such therapies. For example, DBS may include stimulation of the thalamus or basal ganglia and may be used to treat disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

However, understanding of the therapeutic mechanisms of action remains elusive. The stimulation parameters, electrode geometries, or electrode locations that are best suited for existing or future uses of DBS also are unclear.

For conducting a therapeutic stimulation, a neurosurgeon can select a target region within the patient anatomy, e.g., within the brain for DBS, an entry point, e.g., on the patient's skull, and a desired trajectory between the entry point and the target region. The entry point and trajectory are typically carefully selected to avoid intersecting or otherwise damaging certain nearby critical structures or vasculature. A stimulation electrode leadwire used to provide the stimulation to the relevant anatomical region is inserted along the trajectory from the entry point toward the target region. The stimulation electrode leadwire typically includes multiple closely-spaced electrically independent stimulation electrode contacts.

The target anatomical region can include tissue that exhibit high electrical conductivity. For a given stimulation parameter setting, a respective subset of the fibers are responsively activated. A stimulation parameter may include a current amplitude or voltage amplitude, which may be the same for all of the electrodes of the leadwire, or which may vary between different electrodes of the leadwire. The applied amplitude setting results in a corresponding current in the surrounding fibers, and therefore a corresponding voltage distribution in the surrounding tissue. The complexity of the inhomogeneous and anisotropic fibers makes it difficult to predict the particular volume of tissue influenced by the applied stimulation.

A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved via tedious and variable trial-and-error, without visual aids of the electrode location in the tissue medium or computational models of the volume of tissue influenced by the stimulation. Such a method of parameter selection is difficult and time-consuming and, therefore, expensive. Moreover, it may not necessarily result in the best possible therapy.

Systems have been proposed that provide an interface that facilitates parameter selections. See, for example, U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety.

Such systems display a graphical representation of an area within which it is estimated that there is tissue activation or volume of activation (VOA) that results from input stimulation parameters. The VOA can be displayed relative to an image or model of a portion of the patient's anatomy. Generation of the VOA is based on a model of fibers, e.g., axons, and a voltage distribution about the leadwire and on detailed processing thereof. Performing such processing to provide a VOA preview in real-time response to a clinician's input of parameters is not practical because of the significant required processing time. Therefore, conventional systems pre-process various stimulation parameter settings to determine which axons are activated by the respective settings.

SUMMARY

According to an example embodiment of the present invention, a method for determining an estimated VOA for particular stimulation parameter settings includes analysis of modeled neural elements as a whole, analysis of a voltage field at those neural elements, and determination of a threshold voltage or activating function at the neural elements at which the neural elements are activated for a given parameter setting. However, particularly where a leadwire is used that allows for different amplitudes to be applied at different ones of the electrodes of the leadwire, the estimated VOA based on the threshold universally applied to all of the neural elements, may be inaccurate.

Accordingly, in an example embodiment of the present invention, a system and method includes a processor that analyzes a combination of two or more shape parameters that characterize electrical attributes of an anatomical region, on a neural element by neural element basis, that result from a particular stimulation setting. The shape parameters relate to an electrical profile along a trajectory of a neural element. For example, as described below, the shape parameters, in an example, characterize the voltage along the neural element or the activating function along the neural element. The neural element can be, for example, a fiber or a cell with an axon, and is hereinafter referred to as a fiber. The shape parameters may differ between different ones of the fibers surrounding the stimulation leadwire. The system is configured to determine, for each such combination of shape parameters, a respective threshold stimulation parameter setting at which a fiber having the respective combination of shape parameters is activated. The system can store the data, and later reference the data for a stimulation setting proposed by a clinician to obtain the thresholds for respective fibers at that proposed stimulation setting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1:
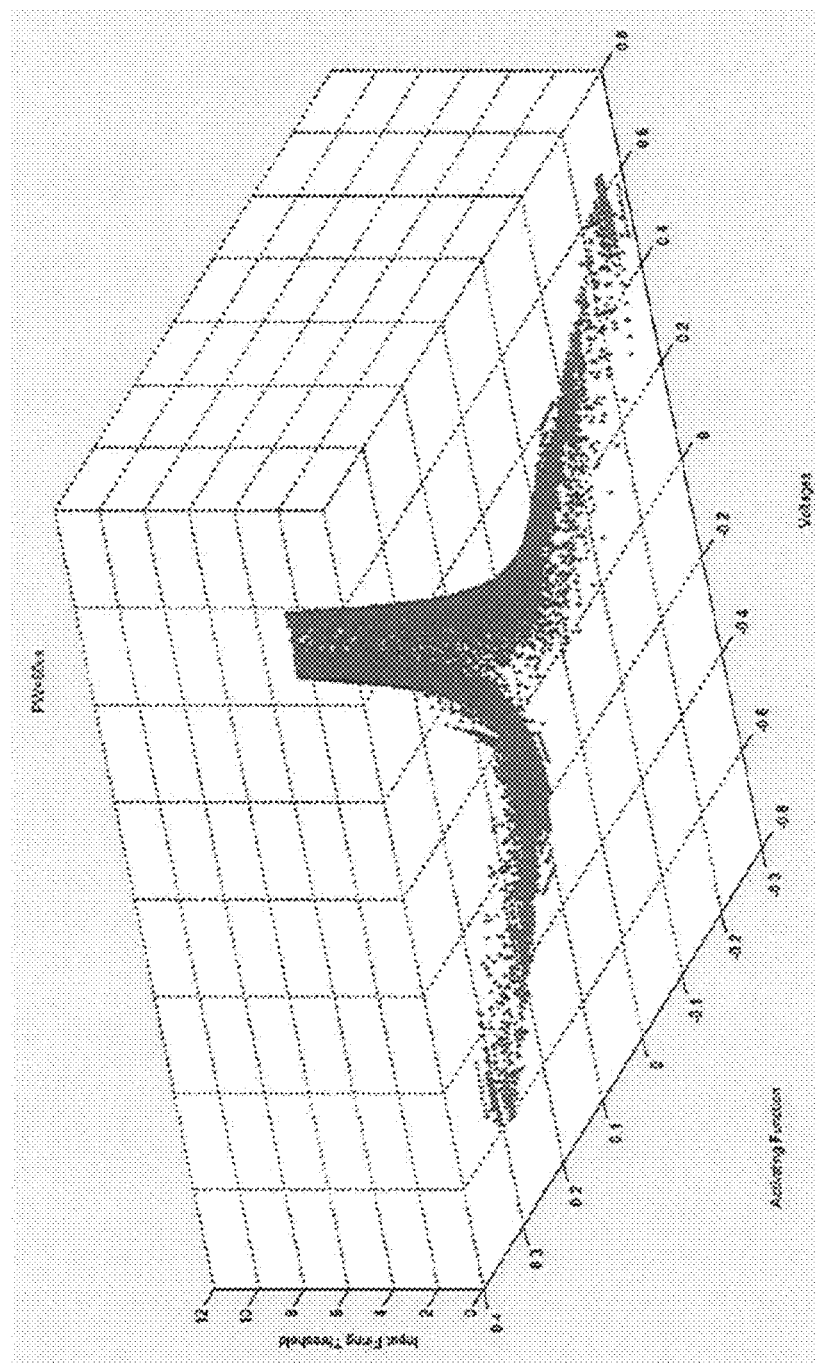
FIG. 1 is a graph of values for peak voltage and peak activating function (two shape parameters) recorded against respective firing threshold values, according to which a lookup table can be populated, according to an example embodiment of the present invention.

In an example embodiment of the present invention, the system can store shape parameter and threshold data in a look-up table (LUT). Thereafter, when a clinician inputs a proposed parameter setting of the stimulation leadwire, the system can determine the values of the same combination of shape parameters for each of the fibers, and then find the stimulation setting threshold value corresponding in the LUT to the shape parameter combination determined for the fiber. If the input stimulation setting meets the threshold value obtained from the LUT, the processor graphically indicates that the respective fiber is activated by the VOA generated and displayed based on this fiber by fiber analysis.

In an example embodiment, the processor can initially calculate the threshold data for each possible combination of shape parameters. Alternatively, the processor can initially calculate first threshold data for a modeled subset of all possible combinations of shape parameters, populate the LUT with the first calculated threshold data, and further populate the LUT with threshold data for other combinations of shape parameters that are not modeled by interpolation and/or smoothing of the data concerning the modeled shape parameters. Any suitably appropriate interpolation and/or smoothing method can be used. Additionally or in an alternative embodiment, the processor can further populate the LUT with threshold data for other combinations of shape parameters, calculated not by direct modeling, but rather by extrapolation based on the existing directly modeled data concerning the modeled shape parameters. Any suitably appropriate extrapolation method can be used.

Alternatively, the processor can initially calculate, and populate the LUT with, the threshold data for a modeled subset of all possible combinations of shape parameters. Subsequently, in real time response to clinician input parameters, the system can, for each of a plurality of fibers, determine the respective combination of shape parameters, and obtain the threshold stimulation parameter value identified in the LUT for the respective combination of shape parameters if there is one, and, otherwise, obtain the shape parameter values and respective threshold values of the LUT nearest to those determined for the respective fiber and interpolate, smooth, and/or extrapolate from those values to obtain the threshold value for the combination of shape parameters for the respective fiber. The obtained shape parameter values can be the nearest single combination of shape parameters and its corresponding threshold value or can be a nearest set of shape parameter combinations and their corresponding thresholds.

In an example embodiment of the present invention, the system initially performs an extrapolation to populate the LUT. Subsequently, in real-time, the system obtains values from the LUT, which values can include the extrapolated values, and performs an interpolation and/or smoothing on such values (e.g., where an exact match is not already included in the LUT), to obtain the relevant information.

In yet another example embodiment, the system performs a two step extrapolation to populate all data within the convex hull, where in the first step, the hull is drawn around an outer boundary of the populated data, and in the second step, the hull is drawn within the data, so that the holes within the interior of the data are considered to be outside the convex hull.

Figure 5:
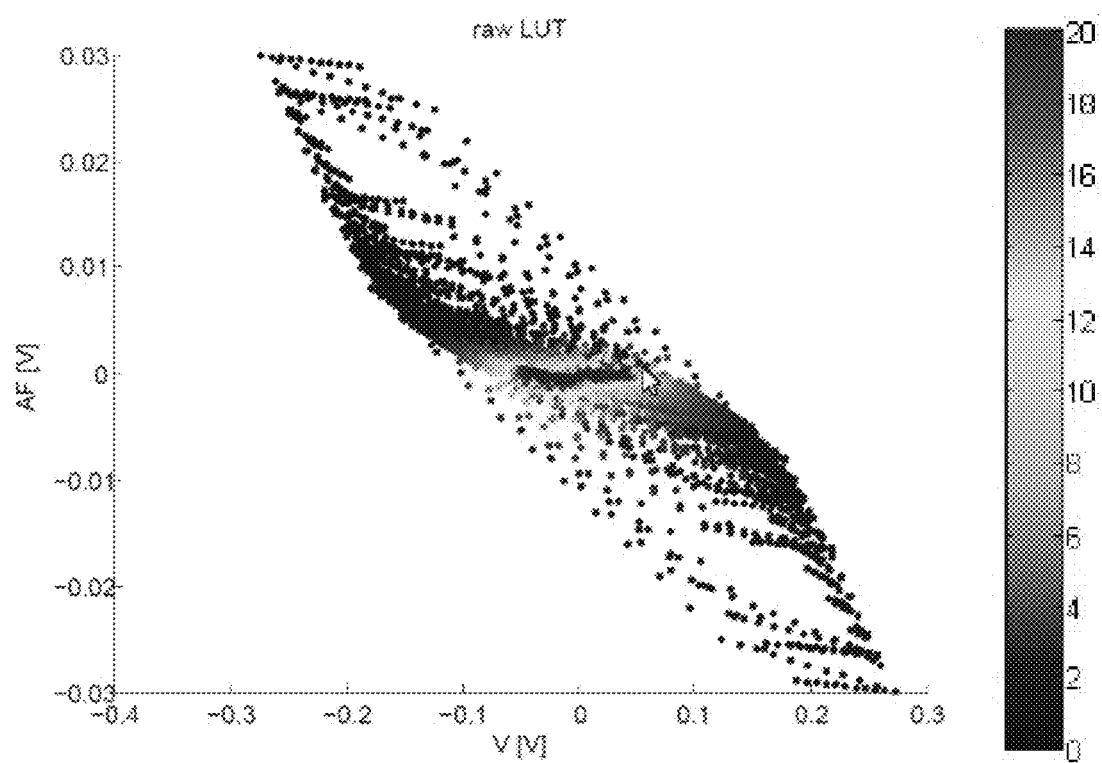
FIG. 5 is a graph, prior to interpolation and extrapolation, of values for voltage and activating function with plotted components representing, by color and intensity, the required threshold for the respective combined voltage and activating values at which the components are respectively plotted.

For example, FIG. 5 shows modeled threshold values represented by color and intensity (deep blue representing a low threshold value and deep red representing a high threshold value) plotted against some intersections of voltage and activating function values (two example shape parameters), no threshold values having been modeled for many of the intersections of the represented activating function and voltage values. An overall lip shaped convex hull is formed by the plotted threshold values. In an example embodiment, based on the behavior of the plotted threshold values within the convex hull, the system extrapolates to apply rules to the intersection of activating function and voltage values external to the convex hull and obtain values at those hull external intersecting values.

In an example embodiment, the system further interpolates and/or smoothes the values within the hull to further fill in threshold values in the holes within the hull. Such interpolation and/or smoothing can occur before or after the extrapolation, as mentioned above. In an example embodiment the interpolation and/or smoothing can be performed after the extrapolation, the extrapolated values providing further input data for a better smoothing in the interpolation and/or smoothing phase. In an example embodiment of the present invention, as mentioned above, the system can be configured to initially populate extrapolated values of the LUT, and later perform interpolation in real time where the LUT does not include a threshold value for a particular combination of shape parameters for a given fiber.

In an alternative example embodiment, as noted above, the system performs a two-step extrapolation. Referring again to FIG. 5, after extrapolating values to populate the graph outside the lip-shaped convex hull, new convex hulls can be drawn within the graph, so that the holes of missing data within the lip-shape are located external the newly considered convex hulls. The data surrounding the hulls are then considered, so that, based on the behavior of those surrounding plotted threshold values, the system extrapolates to apply rules to the intersection of activating function and voltage values external to the convex hulls, i.e., within the holes, and obtain values at those hull external intersecting values, thereby populating the remaining portions of the graph.

Figure 6:
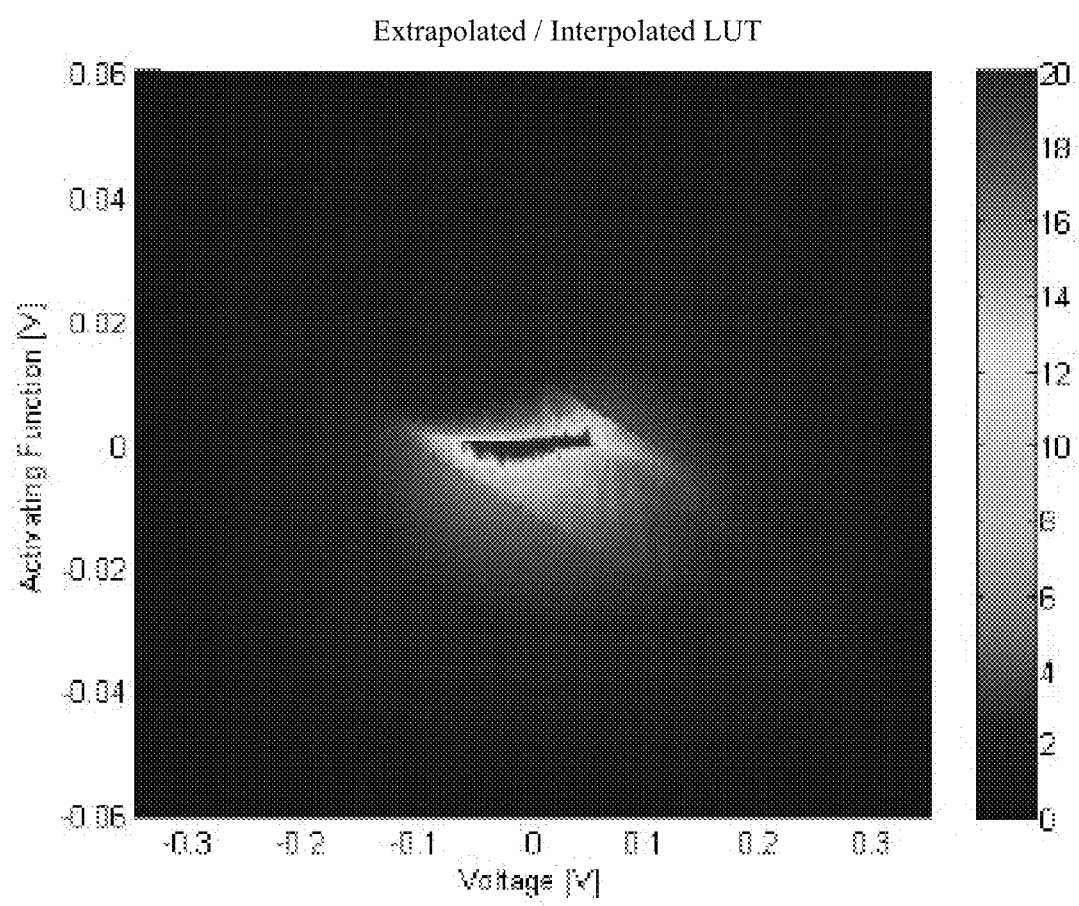
FIG. 6 shows a graph after extrapolation and interpolation of the plotted components of FIG. 5.

FIG. 6 shows the graph of FIG. 5 modified to be populated with extrapolated and/or interpolated values.

In an alternative example embodiment of the present invention, the system can generate an equation or algorithm in the form of Threshold=f(SP1, SP2) based on the threshold data determined for various shape parameter combinations, where SP1 is a first shape parameter and SP2 is a second shape parameter. According to an example embodiment in which more than two shape parameters are used, the function or method can be in the form of Threshold=f(SP1, SP2 ... SPN). Thereafter, when a clinician inputs a stimulation parameter, the system can determine, for each of a plurality of fibers, the shape parameters for the input stimulation parameter and obtain the threshold corresponding to the shape parameters using the function. The system can then output a VOA based on the thresholds determined for those fibers.

In an example embodiment of the present invention, the analyzed shape parameters can be a combination of a peak voltage across the fiber and a peak of value of an activating function across the fiber. The activating function can be a second difference of the voltage values. For example, for each of the fibers, the system can plot or determine the voltages and the second difference values of the voltages, and select the respective peak values of each along the respective fiber. See for example the '330, '312, '340, '343, and '314 applications, which refer to a Finite Element Analysis (FEA) program, e.g., Comsol, which can be used to model a voltage field for a given electrode contact combination. The system can then find the input stimulation amplitude parameter at which the respective fiber is first activated. For example, the system can initially determine the fiber's reaction to a low amplitude, and incrementally increase the amplitude until it is determined that the fiber would be activated by the applied stimulation. For example, a software package such as NEURON can be used to determine the stimulation amplitude at which the respective fiber fires. The system can record the determined amplitude as the threshold for the respective pair of shape parameters, i.e., peak voltage and peak of second difference of the voltages. FIG. 1 shows an example graph of values for peak voltage and peak activating function (second difference) recorded against respective firing threshold values.

Thereafter, during use of the system by a clinician, the system can, on a fiber by fiber basis, (a) determine the voltage distribution and second difference values of those voltages (according to other embodiments, different shape parameters can be determined), (b) select the peak of those values along the respective fiber, (c) look up the threshold amplitude previously recorded by the system for those peak values, (d) and set the fiber as being activated if the input amplitude setting meets the threshold and otherwise as not being activated. The system can then graphically display a VOA including all of the fibers whose corresponding thresholds are at or below the input amplitude setting. It is noted that different steps can be performed by different terminals/processors. For example, a first terminal/processor can execute software for determining the thresholds. A second terminal/processor can be operated by a clinician to input the amplitude parameter and can select the previously recorded thresholds to determine whether the respective fibers would be activated at the input amplitude and accordingly output a VOA.

Figure 2:
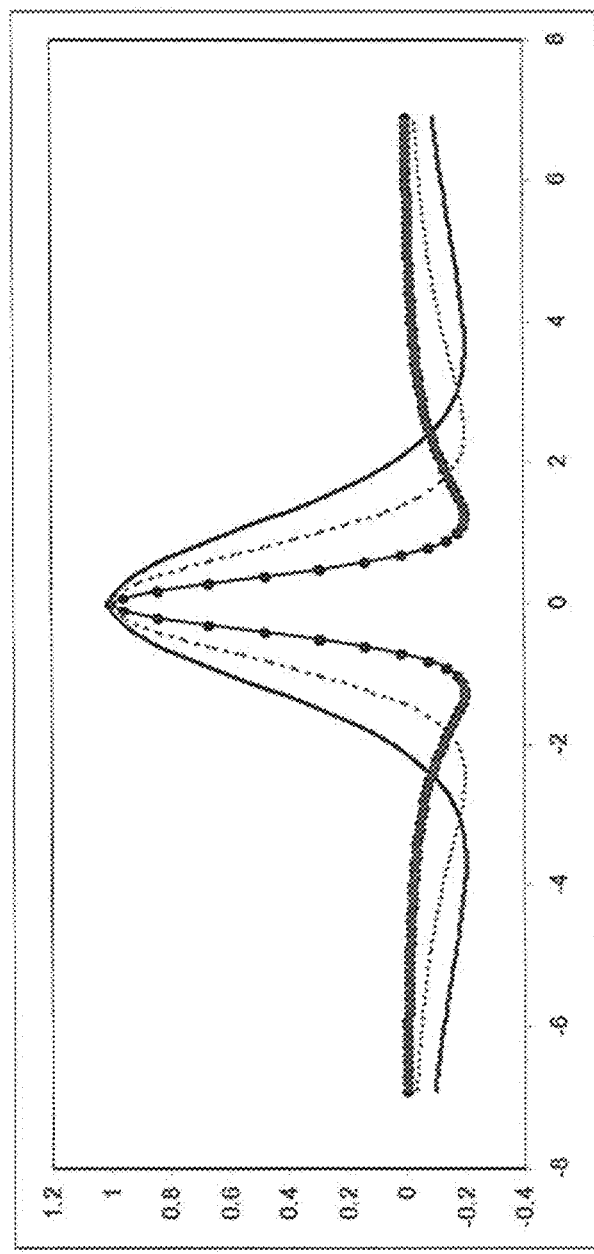
FIG. 2 includes second difference (i.e., activating function) graphs, showing a correspondence between fiber distance and graph shape.

The peak voltage and second difference value can characterize very well the shape information concerning the distribution of electrical values of the respective fibers because they represent the height and spread of the value distribution, which is also dependent on distances of the respective fibers from the electrodes. For example, FIG. 2 shows graphs of the values of the second difference of voltages plotted against nodes of a respective fiber, where the center node is represented by the value of 0 on the abscissa and where each graph corresponds to a respective fiber. The second difference values of FIG. 2 have been normalized to peak at 1. (However, normalization can be to other values instead.) It is noted that, while the graphs can represent stimulation at negative amplitude, such that the voltages can all be below 0, the second difference values can still include values both below and above 0. The graph represented by the plain solid line corresponds to a fiber that is furthest from the leadwire, of the three fibers represented by the graphs in the figure. The graph represented by the dashed line corresponds to a fiber that is between those fibers of the three that are closest and farthest from the leadwire. The graph represented by the dotted solid line corresponds to the fiber of the three that is closest to the leadwire. It can be seen that the closer the fiber is to the leadwire, the less the spread of the graph, which spread is characterized by the peak voltages and second difference values.

In other example embodiments, surrogate shape parameters can be used for characterizing a fiber. For example, since electrical values at a fiber can be dependent upon distance from electrical source, the distance can be a surrogate value for a shape parameter. In an example embodiment, a plurality of shape or other parameters can be used to characterize a fiber. In an example embodiment, different parameters are differently weighted in a function whose output is used as the characterization of the fiber. For example, weighted parameters of a fiber can include, voltage, current density, distance, some activating function, etc.

In an example embodiment of the present invention, the shape parameters characterizing the respective fibers for which the system initially determines the respective thresholds to be recorded are those prevalent at the fibers at unit amplitude, e.g., unit current or unit voltage, for example, where the sum of all amplitudes of all of the electrodes of a given polarity of the leadwire is 1, i.e., they have a combined total magnitude of 1. Although all recorded shape parameter combinations are taken at a combined unit current or voltage, various shape parameter combinations are recorded because of different ratios at which the combined unit current or voltage are applied to the various electrodes of the leadwire. For example, where a leadwire includes four electrodes, a first shape parameter combination can be recorded for an equal distribution of 25% of the unit current or voltage at each of the electrodes, and a second shape parameter combination can be recorded for a distribution of 50%, 25%, 12.5%, and 12.5%. After the shape parameters extant at unit current or voltage are obtained, the system can incrementally increase the applied current or voltage, but at the same ratio of distribution to the electrodes, and can record, for each of the fibers, the, for example, total, current or voltage value at which the respective fiber is activated. Subsequently, when the clinician inputs stimulation parameters, the system can similarly, for each of the fibers, determine the shape parameter combination values at a unit total amplitude with the same electrode distribution ratio as that of the clinician's input values, look up the recorded threshold stimulation amplitude for the respective shape parameter combination values, and determine whether the fiber would be activated by the clinician's input amplitude by comparing the input amplitude to the recorded threshold stimulation amplitude.

Figure 3:
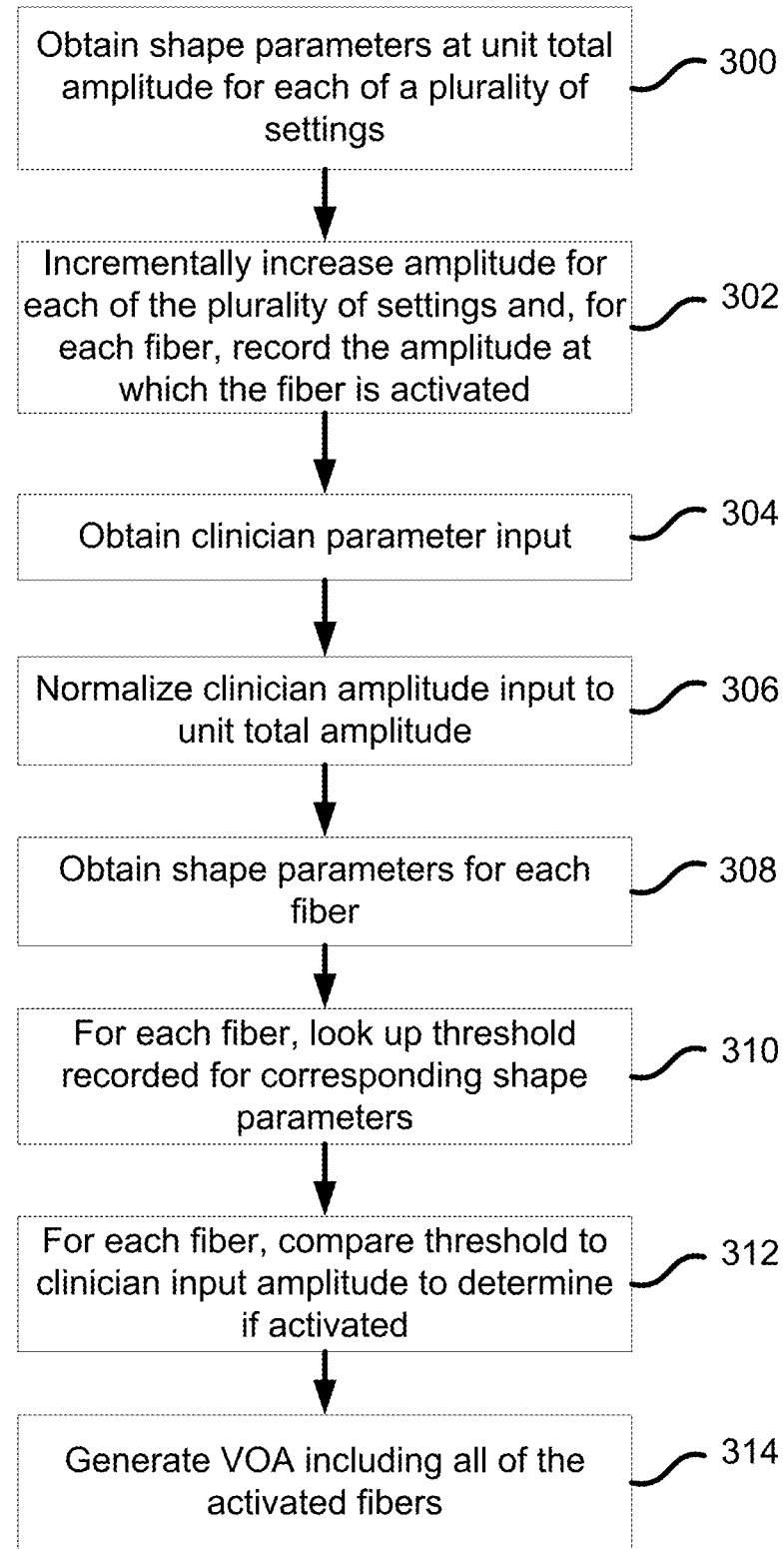
FIG. 3 is a flowchart that illustrates a method for generating a VOA, according to an example embodiment of the present invention.

FIG. 3 is a flowchart that shows steps for determining an estimated VOA for a clinician's input stimulation parameters, according to an example embodiment. At step 300, the system and method obtains shape parameters at until total amplitude for each of a plurality of fibers, for each of a plurality of settings. At step 302, the system and method incrementally increases the amplitude for each of the plurality of settings, and, for each of the fibers, records the amplitude at which the respective fiber is activated. It is noted that step 300 need not be performed completely for all of the plurality of settings prior to performance of step 302. Instead, step 302 can be performed for any one setting immediately following performance of step 300 for that respective setting. It is also noted that the plurality of settings for which steps 300 and 302 are performed need not include all possible settings, as explained above.

At step 304, the system and method obtains clinician parameter input, including an amplitude setting. At step 306, the system and method normalizes the clinician amplitude input to a normalization value, e.g., unit total amplitude.

At step 308, the system and method obtains shape parameters for each fiber at the normalized clinician amplitude input. At step 310, the system and method, for each fiber, looks up the threshold recorded for the shape parameters corresponding to the respective fiber. At step 312, the system and method, for each of the fibers, compares the obtained respective threshold to the clinician input amplitude to determine whether the fiber is estimated to be activated at the clinician input amplitude. It is noted that step 308 need not be performed completely for all of the plurality of fibers prior to performance of step 310, and that step 310 not be performed completely for all of the plurality of fibers prior to performance of step 312. Instead, step 310 can be performed for any one fiber immediately following performance of step 308 for that respective fiber, and step 312 can be performed for any one fiber immediately following performance of step 310.

At step 314, the system and method generates or updates a VOA based on the activated fibers.

It is noted that different steps illustrated in FIG. 3 can be performed by different processors and terminals. For example, a set-up system can perform steps 300 and 302, which can be time intensive. The results can be loaded on a memory device at, and/or for access by, a second processor and terminal at which a clinician may input parameters for which the processor can access the previously stored results to determine and output the VOA.

Figure 4:
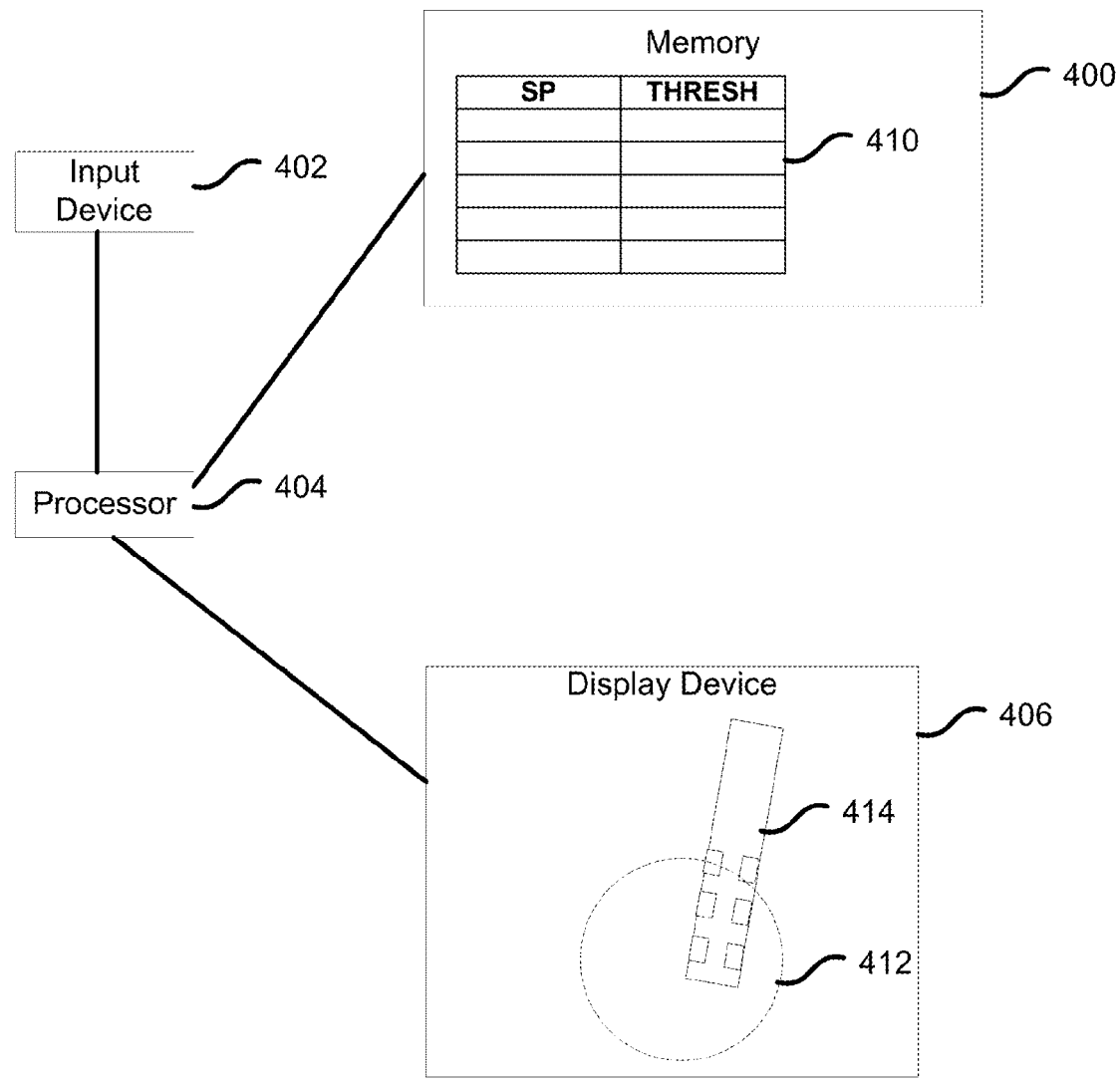
FIG. 4 is a diagram that illustrates a system according to an example embodiment of the present invention.

FIG. 4 shows a system according to an example embodiment of the present invention. One or more LUT(s) 410 are stored in a memory 400. A clinician can input, via an input device 402, parameter settings, including amplitudes for one or more electrodes of a leadwire. A processor 404 can look up, in the LUT(s) 410, threshold values for each of a plurality of fibers surrounding the leadwire to determine which of the respective fibers are estimated to be activated at the clinician input parameters. The processor can output a VOA 412 in a graphical user interface (GUI) presented in a display device 406. The VOA can be displayed relative to a model of the leadwire 414.

It is noted that the recorded thresholds can be the amplitude thresholds directly or some surrogate value. For example, thresholds can be recorded in terms of current density or another electrical parameter.

Settings other than amplitude, such as pulse width, may affect activation. Accordingly, the system can further determine the threshold of a fiber having certain shape parameters for a particular combination of one or more of such other settings. For example, different thresholds can be recorded for a fiber for different pulse widths. In an example embodiment, the system can initially run a simulation for each pulse width allowed by the software to find the respective thresholds at which the respective fibers having respective shape parameter combinations first fire for each such pulse width. Alternatively, the system can initially determine such thresholds for a subset of the possible pulse widths, and then extrapolate and/or interpolate the data to obtain thresholds for other pulse widths that have not been simulated. All such data can be recorded for later threshold lookup in response to clinician input of an amplitude setting at a particular pulse width. Alternatively, as noted above interpolation may be performed in real-time. In an example embodiment, a single LUT stores the threshold data for all combinations of shape parameter combinations and pulse widths. Alternatively, a separate LUT is stored per pulse width, which can be more efficiently processed in response to clinician input of an amplitude setting, by implementing a two-step process of initially selecting an LUT based on pulse width, and then finding the thresholds for the fibers in the selected LUT. According to this latter embodiment and according to the embodiment in which the system does not simulate all possible pulse widths, but rather extrapolates and/or interpolates data for difference pulse widths, the system can initially record LUTs for respective ones of a subset of possible pulse widths, and then extrapolate and/or interpolate from the data of various ones of the LUTs to obtain new LUTs for non-simulated ones of the possible pulse widths.

Aside from pulse width, the data can be further broken down into other groups of data. For example, in an example embodiment, the system further separately stores data for cathodic and anodic arrangements. In this regard, each fiber can be separately characterized as activated by either the cathode or anode, and the appropriate data accessed to obtain its respective threshold. For example, where present clinician settings are such that a particular fiber is affected by the cathode, threshold data for a cathodic arrangement is accessed, and vice versa.

In an alternative example embodiment, whether cathodic or anodic data is accessed to obtain the threshold information is determined by the arrangement as a whole, rather than on the fiber by fiber basis described above. According to this example embodiment, where the IPG can is assigned as the sole anode and the cathodes are all on the leadwire, the configuration is treated on a whole as cathodic, and cathodic data is accessed to determine the threshold for all of the fibers. Other arrangements can be considered anodic arrangements. This described characterization of arrangements as anodic or cathodic is exemplary, and other factors can be used to characterize an arrangement as cathodic or anodic.

While voltage and activating function have been described as an shape parameter combination, other shape parameters can be used instead or in addition. Other shape parameters can include, for example, a windowed activating function, a transmembrane potential $V_m$ (see Warman et al., "Modeling the Effects of Electric Fields on nerve Fibers: Determination of Excitation Thresholds," IEEE Transactions on Biomedical Engineering, Vol. 39, No. 12, pp. 1244-1254 (December 1992), the entire content of which is hereby incorporated by reference herein), and a distance or effective distance function (see Butson et al., "Current Steering to Control the Volume of Tissue Activated During Deep Brain Stimulation," Brain Stimul. 2008 January; 1(1): 7-15, the entire contents of which is hereby incorporated by reference herein; see also Butson et al., "Role of Electrode Design on the Volume of Tissue Activated During Deep Brain Stimulation," J. Neural Eng. 2006 March; 3(1): 1-8, published online on Dec. 19, 2005, the entire contents of which is hereby incorporated by reference herein). It is further noted that a weighted combination of a plurality of parameters, e.g., parameters described above, can be used as a shape parameter.

The generation of a VOA, including the necessary modeling and look-ups on a fiber by fiber basis, as described above may require more processing time than generation based on an estimation for all fibers as a whole. Therefore, in an example embodiment of the present invention, the system and method provide VOA information in a piecemeal manner to quicken an initial response time to a clinician's input parameters. To do so, the system can initially determine and display a VOA based on threshold values for a subset of the fibers, and incrementally sharpen the VOA by subsequently determining the threshold values for more of the fibers. For example, the first displayed VOA can be based on threshold values of every fourth fiber, a second displayed VOA can be based on threshold values of every second fiber, etc. In an example embodiment, the described increase to the spatial resolution can be performed selectively at the VOA boundary as determined by the lower resolution, because it may be assumed that all fibers within the boundary determined by the lower resolution are also activated. For example, a first displayed VOA can be based on threshold values of every fourth fiber, a second displayed VOA can be based on the first displayed VOA and the threshold values of every second fiber that is in between two adjacent discordant fourth fibers, etc.

In an example embodiment, the system uses another form of piecemeal output of the VOA, which can be used by the system as an alternative to the above-described method or additional to it, by which the system first performs a linear estimation to generate the first displayed VOA, and then uses a non-linear model of the fiber to update the display of the VOA. For example, after use of the linear method by which to quickly provide a display of a VOA, the system uses a very accurate, but slower, non-linear method that uses numerical integration for refining the displayed VOA In an example embodiment of the present invention, a further method for increasing response time, which can be used instead of or in addition to the above-described method of initially displaying a coarse VOA, can include initially finding an approximate grid size of the VOA and then finding all of the threshold values within the grid (for example for all fibers or, as described above, initially for a subset of the fibers within the grid and then incrementally for more and more of the fibers). For example, the system can store for each of a plurality of amplitude values (e.g., of a combination of all active electrodes of the leadwire), a respective expected grid size. In response to the clinician's amplitude input, the system can determine whether any of the fibers at a perimeter of the grid size stored in association with the clinician's amplitude input is estimated to be fired. If none is estimated to be activated, the system reduces the grid size, until at least one fiber at the perimeter is estimated to be activated, and determines which of the remaining fibers within the grid are estimated to be activated, for example all of the remaining fibers on a fine granular basis, or initially coarsely and then incrementally more finely, as described above.

In an example embodiment, as soon as the system determines that any of the fibers at the perimeter of the associated grid is estimated to be activated, the system can obtain a larger grid, and again determine whether any of the fibers at the perimeter is estimated to be activated. The system can repeat this until a grid is found in which none of the fibers at the perimeter thereof is estimated to be activated, and can then determine, for each of the fibers within the grid (or a coarse subset thereof), whether the respective fiber is estimated to be activated, the combination of all of the fibers estimated to be activated forming the VOA.

In an example embodiment of the present invention, a Marching Squares or Cubes algorithm can be used to generate the VOA. For example, after obtaining the threshold values of the modeled fibers, the system can apply the Marching Cubes algorithm to determine the locations between the fibers having the necessary threshold for activation at the clinician's input settings. In this regard, although individual fibers are modeled and evaluated, the actual location of fibers in an anatomical region may be unknown. Therefore, all of the space surrounding the leadwire is ultimately treated as potential fiber locations, and the system determines where activation would occur in such space if fibers were included in the space. For each fiber, this can be performed for each adjacent surrounding fiber, e.g., each of four fibers surrounding the center fiber and offset at 90° from each other. That is, locations between a fiber and each of its four surrounding fibers, which locations meet the threshold, can be determined. A line drawn between such threshold points surrounding the center fiber can form a boundary.

In a variant of this embodiment, the system and method can first find each pair of adjacent fibers whose threshold values are respectively above and below the actual input value, and can then apply the Marching Cubes algorithm selectively to only such pairs of adjacent fibers to obtain the VOA. Such a selective application of the Marching Cubes algorithm may speed response time. Stated otherwise, the system and method can initially search for those cubes of a grid whose vertices meet exactly (as opposed to exceeding or being below) the desired threshold, and can selectively apply the Marching Cubes algorithm to only those cubes.

In an example embodiment of the present invention, where the settings of the leadwire electrodes are rotationally symmetric about the leadwire, the system and method can determine a portion of the VOA at one side of a plane that longitudinally intersects the center of the leadwire along its length, according to one or more of the methods described above (or according to other methods), and can then revolve the result around the leadwire to complete the VOA, instead of performing the calculations, modeling, and/or look-ups for all of the fibers surrounding the leadwire. In this regard, while fibers at different locations may differently react to the same electrode parameters, the inventors have discovered that this is usually so for fibers at different longitudinal locations of the leadwire, but that fibers that are at the same longitudinal location but rotationally offset with respect to the leadwire usually react similarly to the same electrode parameters.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The one or more processors can be embodied in a server or user terminal or combination thereof. The user terminal can be embodied, for example, a desktop, laptop, hand-held device, Personal Digital Assistant (PDA), television set-top Internet appliance, mobile telephone, smart phone, etc., or as a combination of one or more thereof. Specifically, the terminal can be embodied as a clinician programmer terminal, e.g., as referred to in the '330, '312, '340, '343, and '314 applications. Additionally, as noted above, some of the described methods can be performed by a processor on one device or terminal and using a first memory, while other methods can be performed by a processor on another device and using, for example, a different memory. In an example embodiment, the look up tables can even be stored on an implantable medical device (IMD) with which the clinician programmer terminal communicates via a telemetry device.

The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to one or more hardware computer-readable media, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

The above description is intended to be illustrative, and not restrictive. Those skilled in the art can appreciate from the foregoing description that the present invention can be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following listed features. For example, while the descriptions above specifies certain therapies, the above-described features can similarly be applied to other forms of electrode therapy.

What is claimed is:

1. A computer system for generating an estimated volume of activation (VOA), the system comprising:
   a computer processor configured to:
   for each of a plurality of neural elements that are in a vicinity of a leadwire:
   determine a respective threshold activation value; and
   determine whether a user-input stimulation value to be applied to the leadwire meets the respective threshold activation value of the respective neural element; and
   generate a surface structure corresponding to those of the neural elements whose respective threshold activation values have been determined to be met by the user-input stimulation value.

2. The system of claim 1, wherein the leadwire is arranged to provide an anodic stimulation.

3. The system of claim 1, wherein the user-input stimulation value includes one of a current amplitude and a voltage amplitude.

4. The system of claim 1, wherein the user-input stimulation value includes a respective distinct stimulation value for each of a plurality of contacts of the leadwire.

5. The system of claim 4, wherein the respective distinct stimulation values include current values.

6. The system of claim 1, wherein the leadwire is configured to provide a deep brain stimulation (DBS) therapy.

7. The system of claim 1, wherein the leadwire is configured to provide a spinal cord stimulation (SCS) therapy.

8. The system of claim 1, wherein the leadwire is configured to provide an Occipital NS therapy.

9. The system of claim 1, wherein the leadwire is configured to provide a Trigemenal NS therapy.

10. The system of claim 1, wherein the leadwire is configured to provide a peripheral field stimulation therapy.

11. The system of claim 1, wherein the leadwire is configured to provide a sacral root stimulation therapy.

* * * * *